United States Patent [19]

Nakamura et al.

[11] Patent Number: 4,666,269

[45] Date of Patent: May 19, 1987

[54] OPHTHALMOLOGIC APPARATUS

[75] Inventors: Yukitugu Nakamura, Sagamihara; Kyoji Sekiguchi, Kawasaki; Takashi Masuda, Saki, all of Japan

[73] Assignee: Canon Kabushiki Kaisha, Tokyo, Japan

[21] Appl. No.: 801,500

[22] Filed: Nov. 25, 1985

Related U.S. Application Data

[63] Continuation of Ser. No. 520,217, Aug. 4, 1983, abandoned.

[30] Foreign Application Priority Data

Aug. 9, 1982 [JP] Japan .................. 57-138166
Aug. 10, 1982 [JP] Japan .................. 57-138762

[51] Int. Cl.⁴ .............................................. A61B 3/10
[52] U.S. Cl. .................................. 351/212; 351/247
[58] Field of Search ............................. 351/212, 247

[56] References Cited

U.S. PATENT DOCUMENTS

| | | | |
|---|---|---|---|
| 3,248,162 | 4/1966 | Knoll | 351/212 |
| 3,639,043 | 2/1972 | Townsley | 351/212 |
| 3,797,921 | 3/1974 | Kilmer et al. | 351/212 |
| 3,932,030 | 1/1976 | Hasegawa et al. | 351/212 |
| 4,046,463 | 9/1977 | La Russia | 351/212 |
| 4,159,867 | 7/1979 | Achatz et al. | 351/212 |
| 4,256,385 | 3/1981 | Cohen | 351/212 |
| 4,426,141 | 1/1984 | Holcomb | 351/212 |

Primary Examiner—Rodney B. Bovernick
Attorney, Agent, or Firm—Fitzpatrick, Cella, Harper & Scinto

[57] ABSTRACT

An ophthalmologic apparatus including an illuminating light source, an annular index, and an optical system for projecting the index from an infinite distance to a cornea of an eye to be examined, in which the index is formed integrally with the projecting optical system.

18 Claims, 13 Drawing Figures

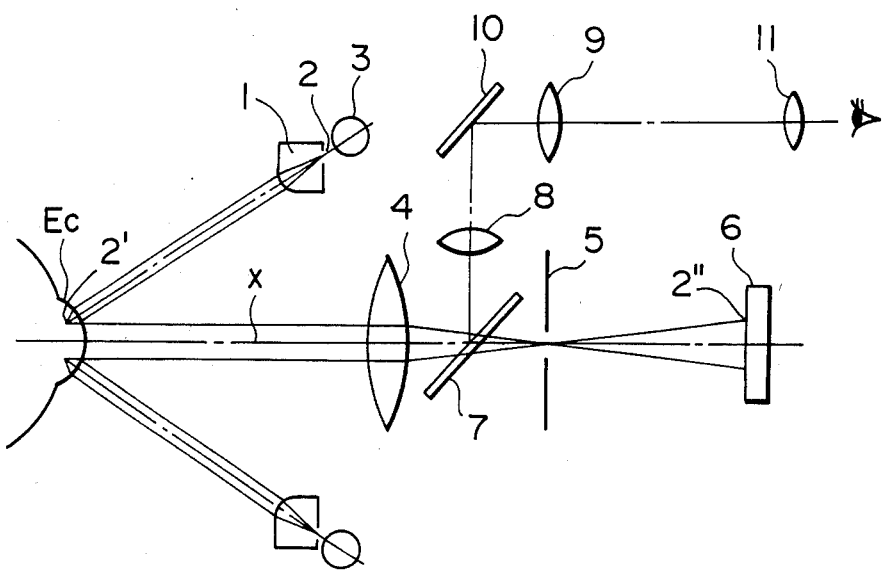
FIG. 1
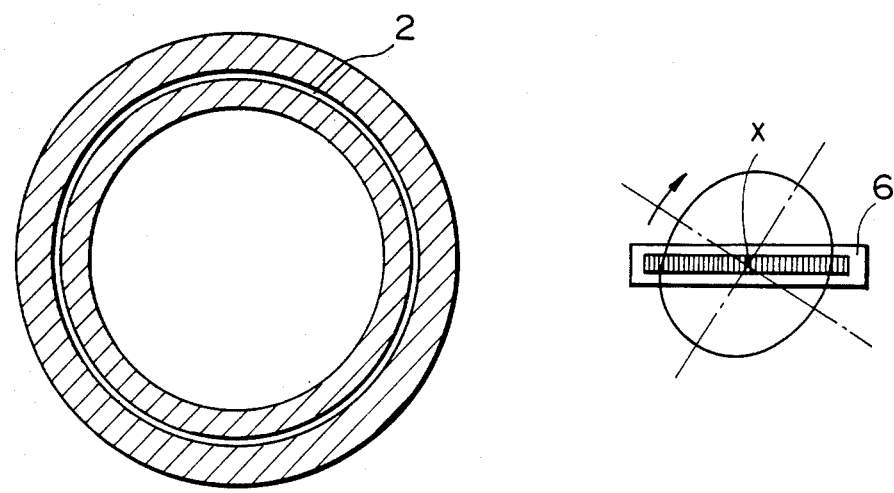
FIG. 2
FIG. 3

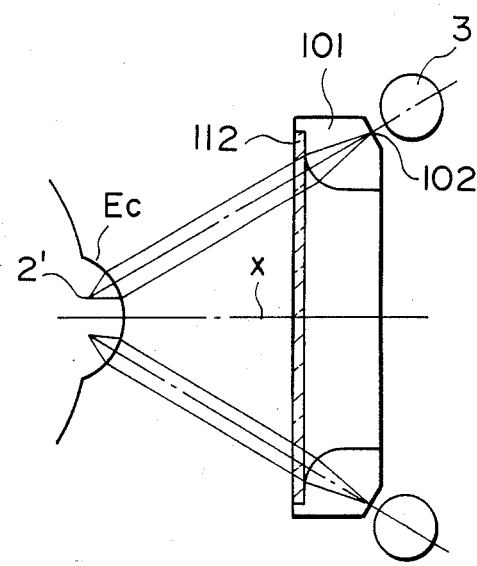
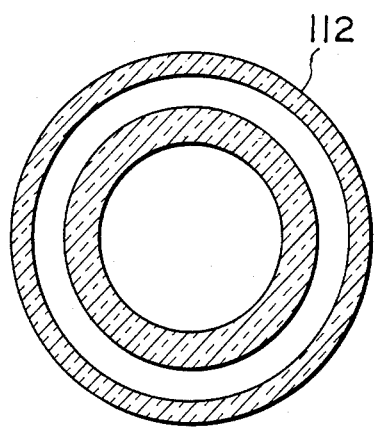
F I G. 4    F I G. 5
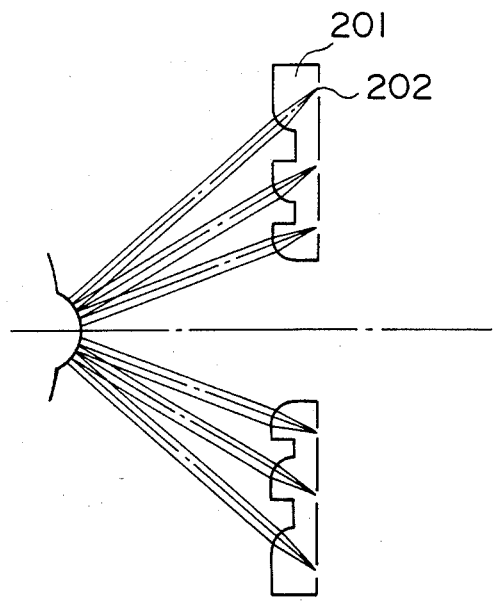
F I G. 6

FIG. 10
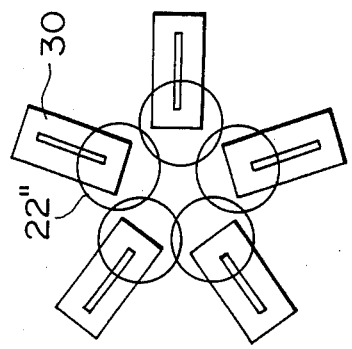
FIG. 13
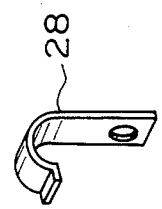
FIG. 9
FIG. 12
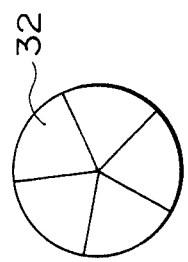
FIG. 8
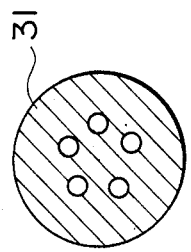
FIG. 11

OPHTHALMOLOGIC APPARATUS

This application is a continuation of application Ser. No. 520,217 filed Aug. 4, 1983, now abandoned.

BACKGROUND OF THE INVENTION

1. Field of the Invention

The present invention relates to an ophthalmologic apparatus adapted for the measurement of radius of curvature or refractive power of a cornea of an eye, degree of astigmatism, base curve of a contact lens etc.

2. Description of the Prior Art

Conventional keratometers, such as Sutcliffe's and Littmann's, project an index onto the cornea of an eye to be examined from the peripheral direction of an objective lens, observe the size of the image reflected by the cornea with a measuring optical system including an image matching system, and determine the radius of curvature or refractive power of the cornea from the amount of displacement of a prism etc. in said image matching system. Such methods however require considerable time for the measurements and inevitably result in an error if the eye to be examined shows rapid movement.

Also Sutcliffe's keratometer can easily identify the distortion of the reflected image caused by corneal astigmatism, tears etc. from the state of the image reflected by the cornea since an index of a circular slit is projected onto the cornea, but errors in the measurements are unavoidable if the relative position between the index and the eye to be examined is not adequate.

On the other hand, Littmann's keratometer can provide exact measurements with limited errors even when the relative position between the index and the eye to be examined is somewhat different from the optimum situation, but is unable to easily identify the state of corneal astigmatism etc. since the index projected onto the cornea of the eye to be examined is only in the direction of a particular meridian.

In order to overcome the aforementioned drawbacks, the present applicant already proposed, in the U.S. patent application Ser. No. 416,355, a structure in which an annular index is projected from an infinite distance onto the cornea of the eye to be examined. The present invention is to provide further improvements on the above-mentioned structure.

SUMMARY OF THE INVENTION

An object of the present invention is to provide an ophthalmologic apparatus for the measurement of corneal shape or contour, which ensures precise alignment, without deviation, between the index and the projecting means therefor with a low production cost and which is free from errors in the measurements even when the distance between the cornea of the eye to be examined and the index is somewhat different from the optimum condition.

Another object of the present invention is to provide an ophthalmologic apparatus enabling easy positioning of the eye to be examined, also enabling the observation whether the reflected image of the cornea is distorted by tears or by corneal astigmatism, and allowing the measurement of the shape of the cornea within a very short time.

BRIEF DESCRIPTION OF THE DRAWINGS

FIG. 1 is a cross-sectional view of a first embodiment of the present invention;

FIG. 2 is a view of a circular slit constituting the index;

FIG. 3 is a schematic view of a detector for the shape of the image reflected by the cornea;

FIG. 4 is a cross-sectional view of a second embodiment of the present invention;

FIG. 5 is a schematic view of protecting members constituting a diaphragm for the projecting optical system;

FIG. 6 is a cross-sectional view of a third embodiment of the present invention;

FIGS. 8 to 10 are schematic views of a mounting member for the light source;

FIG. 11 is a schematic view of a stop;

FIG. 12 is a schematic view of a polarizing prism; and

FIG. 13 is a schematic view of detecting elements.

DESCRIPTION OF THE PREFERRED EMBODIMENTS

Figure 7:
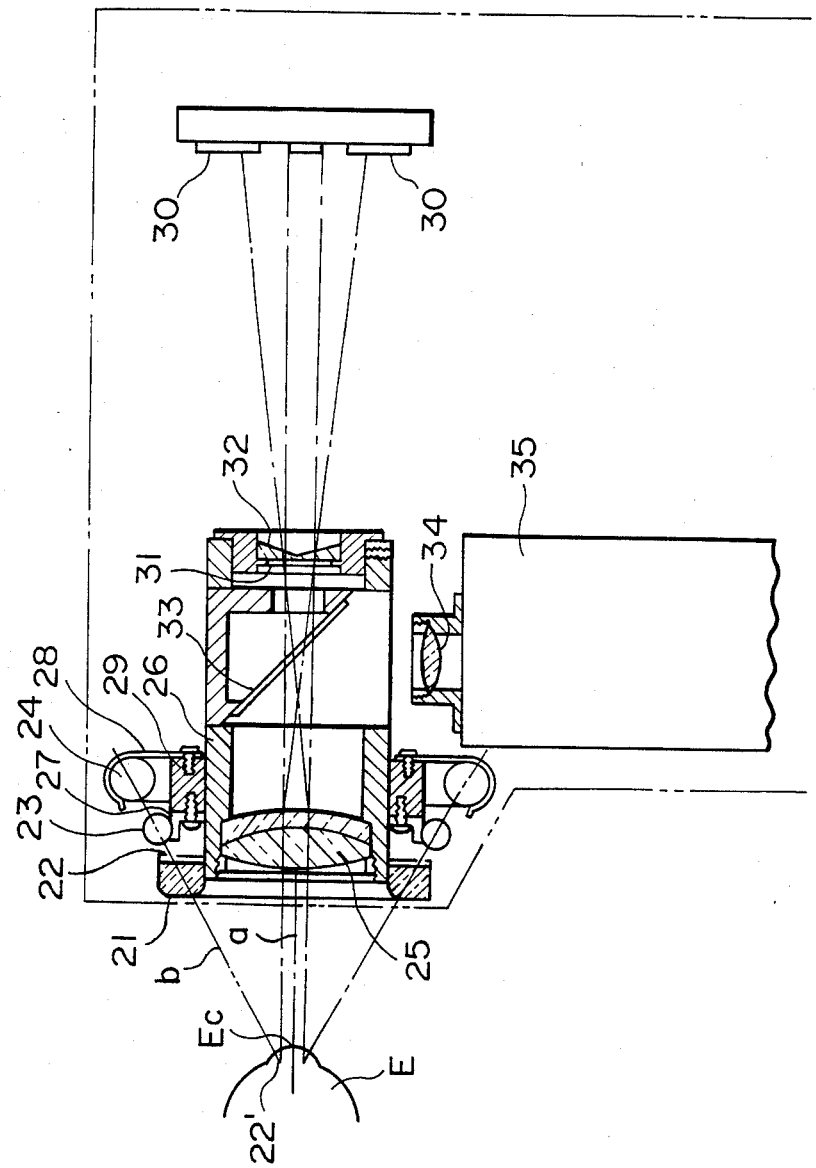
FIG. 7 is a cross-sectional view of an embodiment equipped with a measuring light source and an observing light source.

In FIG. 1, the cornea of an eye to be examined is represented by Ec. An index projecting lens 1 is formed as an annular cylindrical lens at the light-emerging front face, and is provided, on the rear wall positioned close to the rear focal point, with a circular (ring-like) slit 2 constituting the index to be projected as shown in FIG. 2, which is integrally provided by direct vapor deposition or by painting on the projecting lens 1. A light source 3 for illuminating the index 2 is composed for example of a circular strobe light, a circular fluorescent lamp or a plurality of small light sources such as light-emitting diodes arranged on a circle.

Said annular cylindrical lens constituting the projecting lens 1 has a refractive power in each meridian direction but lacks refractive power in the direction perpendicular thereto or the tangential direction.

An objective lens 4 is provided with a stop 5 in the vicinity of the rear focal point and constitutes a telecentric optical system. At the imaging position of the objective lens 4 there is provided a position detecting element 6, which can be composed of a one-dimensional (linear) image sensor such as a CCD, a one-dimensional photodiode array or a two-dimensional (area) image sensor. The aforementioned index projecting lens 1, the circular slit 2 constituting the index to be projected and the circular light source 3 are arranged coaxially around the optical axis x of the objective lens 4, whereby, in a cross section of meridian direction containing the optical axis x as shown in FIG. 1, the light from the index 2 illuminated by the light source 3 is converted, by the annular cylindrical lens of the projecting lens 1, into parallel light beams equivalent to the light beam from an infinite distance and projected onto the cornea.

Due to the convex mirror effect of the cornea Ec, there is formed a corneal reflection image 2' (virtual image) of the index 2. Since the projecting optical system projects a light beam from the infinite distance to the eye to be examined, the dimension of the corneal reflection image 2' does not change even when the distance between the index and the cornea Ec becomes somewhat different from the optimum value.

Also since the imaging optical system for focusing the corneal reflection image 2' on the position detecting element 6 is a telecentric system, the dimension of the projected image 2" of the corneal reflection image 2' on the position detecting element 6 does not change even when the axial working distance between the cornea Ec and the objective lens 4 is varied.

Thus, by the cooperation of the illuminating optical system and the imaging optical system, a slight axial movement of the eye to be examined does not alter the dimension of the corneal reflection image 2' and does not, therefore, lead to an error in the measurement. A completely spherical cornea Ec will provide a completely circular reflected image 2', but in practice said reflected image often appears as an ellipse since the cornea generally has a toric surface.

For this reason, the measurement of the shape of the corneal reflection image 2' requires a system capable of determining the shape of an ellipse.

FIG. 3 shows an embodiment of such measuring system, in which the position detecting element 6, composed of a one-dimensional photodiode array, performs rotary scanning around the optical axis x to electrically determine the major radius, minor radius and axes of the elliptic projected image 2" of the corneal reflection image 2'.

These elliptic data can be utilized for determining the radius of curvature of cornea, and the degree and direction of astigmatism.

Naturally the measuring system is not limited to the above-described one but may be composed, for example, of three one-dimensional photodiode arrays positioned in a determined relationship or of a two-dimensional image sensor for achieving instantaneous automatic measurement.

In order to enable observation of the external appearance of the cornea and of the corneal reflection image upon positioning of the cornea Ec with respect to the measuring system, there may be preferably provided, in the measuring optical path, an observing optical system comprising a beam-splitting mirror 7 such as a half mirror or a dichroic mirror; relay lenses 8, 9; a mirror 10; and an eyepiece lens 11. In case the beam-splitting mirror 7 is composed of a dichroic mirror, a separate light source is preferably provided for emitting a light beam to be guided to the observing optical system through reflection by the beam-splitting mirror 7.

FIG. 4 shows a second embodiment of the present invention with an improved performance of the index projecting optical system.

The light beam for projecting the index 102 constituted by a circular slit onto the cornea is desired to be completely parallel in the meridian direction including the optical axis x. In the present embodiment, therefore, an almost parallel projecting beam is obtained by the use of a multi-order curve in the meridian cross section of the cylindrical lens constituting the light-emerging face of an index projecting lens 101, namely by the use of a specially designed cross section, achieving an effect similar to that of an aspherical lens relative to an ordinary spherical lens. The rear face of the projecting lens 101, bearing the index 102, is made substantially perpendicular to the projecting light beam, thus ensuring efficient entry of the illuminating light beam from the light source 3.

A protecting member 112, composed of a transparent circular flat plate as shown in FIG. 5, is adhered to the projecting lens 101 for protecting the cylindrical lens thereof from scratches, dusts and fingerprints. Said protective member 112 is also provided with an annular transmitting area functioning as a stop or a diaphragm for transmitting the effective projecting light beam and intercepting the unnecessary light beam.

FIG. 6 shows a third embodiment of the present invention adapted for measuring the cornea Ec not only in the central part but also in the peripheral part thereof, wherein an index projecting lens 201 is provided with concentric plural annular cylindrical lenses, and indexes 202 composed of plural circular slits are provided respectively corresponding to the rear focal points of said cylindrical lenses.

FIG. 7 shows another embodiment equipped with a measuring light source and an observing light source, wherein shown are an eye E to be examined; a cornea Ec thereof; a projecting lens 21 composed of the aforementioned annular cylindrical lens; an index 22 composed of a circular slit positioned in the vicinity of the rear focal point of the projecting lens 21; a measuring light source 23, composed for example of a ring strobe, for instantaneously emitting light of high intensity to illuminate the index only at the measurement; and an observing light source 24, composed for example of a circular fluorescent lamp, to be continuously lighted for illuminating the index 22 through the tube of said measuring light source 23.

The projecting lens 21 is fixed on a lens tube 26 supporting an objective lens 25, while the measuring light source 23 and the observing light source 24 are mounted, by means of mounting members 27, 28, on a light source support ring 29, which is in turn fixed, in an axially adjustable manner and coaxially with the optical axis a of the objective lens 25, on said lens tube 26. The index 22 is integrally adhered to the projecting lens 21.

In such index projecting system, the optical axis b of the projecting lens 21 should be precisely aligned with the index, and, in addition, it should preferably be positioned at the center of the measuring light source 23 and the observing light source 24. Particularly in case a ring strobe, giving a narrow circular flash, is employed as the measuring light source 23, the intensity of the projecting light beam will be significantly lost unless such light source is exactly positioned, over the entire periphery, on the optical axis b of the projecting lens 21. For this reason, in the present embodiment, the mounting members 27, 28 for supporting the observing light source 24 are provided with elongated fixing holes to allow adjustment of the eccentricity of the light source. Also a slight axial movement of the light source support ring 29 allows the fixation on the lens tube 26 in such a manner that the optical axis b of the projecting lens 21 is positioned exactly at the center of the light-emitting part of the ring strobe.

Also the measuring light source 23 and the observing light source 24 are fixed by mounting members 27, 28 shown in FIGS. 8 and 9 in such a manner that the illuminating light beam is not eclipsed. For example the observing light source 24 is supported, at several places of the rear wall thereof, by the mounting members 28 as shown in FIG. 9 which are fixed with screws on the mounting ring 29, so that the light beam for illuminating the index is not eclipsed.

On the other hand, the measuring light source 23 is supported, at several points along the internal periphery thereof, by mounting members 27 as shown in FIG. 8, and said mounting members 27 are fixed on the mounting ring 29 in such a manner as not to eclipse the measuring light beam nor the illuminating light beam from the observing light source 24.

As an alternative method, the measuring and observing light sources 23, 24 may be fixed with mounting members composed of a transparent material as shown in FIG. 10 in order to avoid eclipse of the light beams. Through the use of the projecting means explained above, the index 22 illuminated by the observing light source 24 and the measuring light source 23 is projected onto the cornea Ec by the projecting lens 21 as a light beam optically equivalent to that from an infinite distance.

Said projecting light beam forms, by the convex mirror effect of the cornea Ec, a virtual reflected image 22' of the index 22, and the dimension of said corneal reflection image 22' does not change even when the distance between the index 22 and the cornea Ec becomes somewhat different from the optimum value because the projection to the cornea Ec is achieved by a light beam from the infinite distance through the aforementioned projecting system.

The corneal reflection image 22' of the index 22 thus obtained is projected, by the telecentric imaging optical system, onto the photosensitive surface of the detecting element 30 to form an image 22" for measurement. Thus, due to the cooperation of the projecting optical system and the imaging optical system, a slight axial movement of the cornea Ec of the eye to be examined does not alter the dimension of the image 22" of the corneal reflection image 22' and does not therefore give rise to an error in the measurement.

The corneal reflection image 22' becomes completely circular when the cornea Ec is completely spherical, but in practice the corneal reflection image 22' often assumes an elliptic form since the cornea Ec is generally toric because of the presence of astigmatism as explained before. For this reason there is required a measuring system capable of determining the shape of an ellipse in order to measure the form of the corneal reflection image 22'. In the following there will be given an explanation on the measuring system employed in the present embodiment.

Referring to FIG. 7, an objective lens 25 is provided, in the vicinity of the rear focal point thereof, with a stop plate 31, behind which is positioned a polarizing prism 32. Said stop plate 31 is provided, for example as shown in FIG. 11, with five small apertures close to the center, while said polarizing prism 32 is composed, as shown in FIG. 12, of five wedge-shaped prisms bonded together, wherein each aperture of the stop plate 31 corresponds to the center of each wedge-shaped prism of the polarizing prism 32.

The light beam from the corneal reflection image 22', entering the objective lens 25, is guided through the apertures of the stop plate 31 and the polarizing prism 32 in the form of five divided beams, which are focused on the photosensitive surface of the detecting elements for example composed of one-dimensional photodiode arrays. Said detecting elements 30 are arranged in the positions of the focused images 22" of the corneal reflection image 22', for example in a manner shown in FIG. 13.

In an actual keratometer, the detection signal from the detecting elements 30 are electrically processed in a signal processing circuit, not shown, to determine the major and minor radii and the axes of the ellipse constituting the corneal reflection image 22', and the elliptic data thus obtained can be utilized for determining the radius of curvature, degree of astigmatism and angle of direction of astigmatism of the cornea.

The measuring system of the present embodiment detects the corneal reflection image 22' along five meridian directions, but such detection may be effected for example along three meridian directions or with a two-dimensional image sensor.

The observing optical system is composed of a beam splitting mirror 33 such as a half mirror or a dichroic mirror and imaging lens 34 to form an image of the external appearance of the eye E to be examined and of the corneal reflection image 22' of the index 22 on an image taking face of a television camera 35, and said image is constantly displayed on a television monitor, not shown, for observation.

As explained in the foregoing, the present invention provides an index projecting optical system for measuring the corneal shape, which does not alter the dimension of the corneal reflection image even when the distance between the index and the cornea of the eye to be examined becomes somewhat different from the optimum situation, and which is further featured by improved precision and by a lower production cost.

The index projecting optical system of the present invention, when combined with a telecentric imaging optical system and an automatic measuring system utilizing a one-dimensional photodiode array or a two-dimensional image sensor as the detector, contributes an automatic apparatus for measuring the corneal shape which is featured by an improved accuracy and by an enlarged tolerance in the working distance between the measuring apparatus and the cornea of the eye to be examined.

Said apparatus can effect exact measurement even for a movable subject such as an eye of a child, since the required information can be collected within an extremely short time by the flash light from a high-power measuring light source.

Also the operator can observe, in combination with the external appearance of the eye to be examined, a corneal reflection image of a measuring index illuminated by a constantly energized light source, which is different from the measuring light source. The operator can therefore easily adjust the position of the eye, constantly confirm whether the part of the eye to be examined is eclipsed by the eyelid or eyelashes, and also confirm whether the corneal reflection image is distorted by tears or by corneal astigmatism.

We claim:

1. An ophthalmologic apparatus comprising:
   a continuous annular index;
   a continuous annular projecting lens having at least a continuous annular cylindrical surface having a refractive power in each meridian direction but lacking a refractive power in a direction perpendicular thereto, said index being integrally provided on a surface of said projecting lens which includes a focal point of said cylindrical surface, wherein said projecting lens projects said annular index onto the cornea of an eye to be examined by converting rays emitted from said index into parallel rays along a direction inclined relative to an axis of the eye to be examined and in a plane containing each meridian of the projecting lens, and wherein observation and accurate measurement of the cornea shape are effected despite misalignment between the axis of the eye to be examined and the central axis of said annular projecting lens;

position detecting means;

a telecentric optical system for projecting an image of said index reflected by the cornea or said position detecting means; and an observing optical system for observing the image of said index reflected by the cornea.

2. An ophthalmologic apparatus according to claim 1, wherein said index is formed by vapor deposition or by painting on said projecting lens.

3. An ophthalmologic apparatus according to claim 1, wherein said projecting lens has plural continuous annular cylindrical surfaces arranged in coaxial manner about the central axis.

4. An ophthalmologic apparatus according to claim 1, wherein said projecting lens is composed, from the continuous annular cylindrical surface to the focal point in each meridian direction, of the same medium of the same refractive power.

5. An ophthalmologic apparatus according to claim 1, further comprising a transparent protective plate provided on the side of said continuous annular cylindrical surface.

6. An ophthalmologic apparatus according to claim 5, wherein said protective plate has a diaphragm function for intercepting the light from said projecting lens other than the effective light beam.

7. An ophthalmologic apparatus according to claim 1, wherein said index is perpendicular to each projecting optical axis of said continuous annular cylindrical surface in each meridian.

8. An ophthalmologic apparatus according to claim 1, further comprising an illuminating light source of the annular type for illuminating said annular index.

9. An ophtalmologic apparatus according to claim 1, further comprising an illuminating light source for illuminating said annular index and including a measuring light source and an observing light source.

10. An ophthalmologic apparatus according to claim 9, wherein said measuring light source is lighted for a short period with a high intensity upon measurement, while said observing light source is continuously lighted upon observation.

11. An ophthalmologic apparatus according to claim 9, wherein said measuring light source comprises an annular strobe device, and said observing light source comprises an annular fluorescent lamp.

12. An ophthalmologic apparatus according to claim 9, wherein said measuring light source is positioned in the vicinity of said index, and said observing light source is so positioned as to illuminate said index through a tube wall of said measuring light source.

13. An opthalmologic apparatus according to claim 9, wherein said illuminating light source is supported at a part of a tube wall thereof, outside of the effective light beam for illuminating the index.

14. An ophthalmologic apparatus according to claim 9, wherein said illuminating light source is supported by a light transmitting mounting member in order to avoid eclipse of the light beam for projecting the index onto the cornea of the eye to be examined.

15. An ophthalmologic apparatus according to claim 9, wherein said measuring light source and said observing light source are formed integrally.

16. An ophthalmologic apparatus according to claim 15, wherein said index, said projecting means, said measuring light source and said observing light source are fixed while being guided by the outer periphery of a casing of said telecentric optical system.

17. An ophthalmologic apparatus according to claim 1, further comprising an illuminating light source for illuminating said index and means for adjusting the distance between said illuminating light source and said index.

18. An ophthalmologic apparatus according to claim 1, further comprising an illuminating light source of the annular type for illuminating said index, the eccentricity of said illuminating light source being adjustable by displacing said source in the meridian direction.

* * * * *